United States Patent [19]

Amick

[11] Patent Number: 4,505,889

[45] Date of Patent: Mar. 19, 1985

[54] PROTRACTED RELEASE MICROBIOCIDAL ARTICLE FOR AQUEOUS SYSTEMS

[75] Inventor: David R. Amick, Chalfont, Pa.

[73] Assignee: Rohm and Haas Company, Philadelphia, Pa.

[21] Appl. No.: 422,055

[22] Filed: Sep. 23, 1982

[51] Int. Cl.$^3$ ............................................. A01N 25/34
[52] U.S. Cl. ..................................... 424/21; 424/15; 424/35; 206/0.5; 210/764; 43/131
[58] Field of Search ............................ 206/0.5, 524.1; 428/315.5, 305.5, 35; 210/764; 43/131; 239/6, 34, 54, 57; 252/90; 424/15, 35; 427/245

[56] References Cited

U.S. PATENT DOCUMENTS

| | | | |
|---|---|---|---|
| 2,846,057 | 8/1958 | Polin | 206/0.5 |
| 3,605,321 | 9/1971 | Lazarus | 43/131 |
| 3,835,578 | 9/1974 | Basile | 43/132 |
| 3,985,298 | 10/1976 | Nichols | 239/54 |
| 4,063,064 | 12/1977 | Saunders et al. | 424/15 X |
| 4,188,418 | 12/1980 | Livingston | 427/245 |
| 4,218,843 | 8/1980 | Clarke | 43/131 |
| 4,248,913 | 2/1981 | Jakabhazy et al. | 427/245 |
| 4,289,815 | 9/1981 | Lee | 428/35 |
| 4,340,491 | 7/1982 | Lee | 210/764 |

Primary Examiner—Shep K. Rose

[57] ABSTRACT

There is disclosed as an article a water-permeable membrane containing sealed therein a solid particulate microbiocidal composition which is useful in aqueous systems, wherein the composition is produced from a microbiocidal compound having relatively low water solubility or a combination thereof with other microbiocidal compounds having relatively high water solubility to give a combination generally characterized by low water solubility in admixture with an inert, finely-divided water-insoluble solid carrier material. Especially useful are microbiocidal 3-isothiazolones and 2-substituted-1,2-benzisothiazolones having relatively low water solubility, and metal salt stabilized derivatives thereof, admixed with silicaceous diatomaceous earth. These articles afford protracted controlled release of active ingredient and also afford a safer form of the active ingredient heretofore known to be relatively irritating to the skin of man when at high concentration in aqueous solution.

10 Claims, No Drawings

PROTRACTED RELEASE MICROBIOCIDAL ARTICLE FOR AQUEOUS SYSTEMS

This invention relates to microbiocidal articles which are sealed water-permeable membranes containing therein dry solid compositions of microbiocidal compounds having relatively low water solubility or a combination thereof with one or more other microbiocidal compounds to give a combination generally characterized by low water solubility, especially 3-isothiazolones and 2-substituted-1,2-benzisothiazolones (hereafter "isothiazolones"), which have a known tendency to effect skin irritancy to man and to evolve nontoxic gases when provided in aqueous solution at concentrations convenient for shipping, to a method of controlling living microorganisms using the microbiocidal compositions, and to a method for safening isothiazolones and controlling the rate of release.

The isothiazolones are a class of chemical compounds known to possess excellent and useful microbiocidal properties and resistance to common additives and contaminants. Many 3-isothiazolones are disclosed in U.S. Pat. Nos. 3,761,488; 3,849,430; 3,870,795; 4,067,878; 4,150,026; and 4,241,214. U.S. Pat. Nos. 3,517,022; 3,065,123; and 3,761,489 disclose 2-substituted-1,2-benzisothiazolones. U.S. Pat. No. 3,849,430 discloses a method for preparing the isothiazolones.

While the afore-mentioned patents disclose the use of isothiazolones in a variety of microbiocidal end uses, such as, for example, those uses and formulations and compositions disclosed in U.S. Pat. No. 3,761,488 at columns 15–19 and in the actual examples thereafter, isothiazolones are generally made available in combination with a liquid carrier such as water or in aqueous compositions. Column 19, line 66 et seq. discloses that isothiazolones can be taken up or mixed with a finely-divided particled solid carrier, as for example, clays, inorganic silicates, carbonates, silicas and organic carriers. Column 20, line 25 et seq. discloses that a convenient method for preparing a solid formulation is to impregnate the isothiazolone toxicant onto the solid carrier by means of a volatile solvent, such as acetone. However, earlier attempts to produce solid formulations have resulted in formulations which tended to coalesce (or "cake") or to give extremely lightweight particles (or "dusts").

U.S. Pat. No. 4,011,172 discloses chlorine bleaching compounds dissolved in water or other suitable solvent thickened by the addition of particulate thickening agent, for example, silicate materials, water-swellable and water-soluble polyacrylamides and cellulose derivatives, and synthetic clays, the thickened bleaching compounds being contained in a perforated pouch made of plastic material.

U.S. Pat. No. 4,170,565 discloses a substrate article for cleaning fabrics, particularly in an automatic washer, consisting essentially of an effective amount of a surface-active composition of about 5–95% by weight of water-soluble surface-active agent contained between two layers of a water-insoluble, wet-strength substrate, at least one of said layers having an air permeability of at least about 10 ft.$^3$ of air per minute per ft.$^2$ of substrate. Preferred substrates include flexible water-insoluble, wet-strength paper, woven cloth, and non-woven cloth substrates, cellulose ester being mentioned among a list of synthetic fibers, suitable for making non-woven cloths. All of the components mentioned for the surface-active composition, including the surface-active agent, are disclosed to be water-soluble.

U.S. Pat. No. 4,289,815 discloses a pouch for the controlled release of active ingredients into an aqueous medium comprising liquid or solid active ingredients enclosed in a sealed envelop of cold-water insoluble polyvinyl alcohol. The object of the invention described in the patent is to provide pouches for delivery of active ingredients which provide a substantially uniform, controlled "zero-order" release of the active ingredients. This objective is achieved by utilizing cold-water insoluble, gas-impermeable polyvinyl alcohol as the polymeric film for preparing the pouches. The patent further discloses that a wide variety of liquid and solid active ingredients are applicable for use in the pouches, examples of which active ingredients include detergents, bleaches, chlorinating agents, pesticides, bactericides, dyes, drugs, and other chemicals. At column 3, lines 53 et seq., the patent teaches that "in order to establish practical release rates, it is required that the active ingredient exhibit a minimum water solubility" and that the water solubility can range from small water solubility to total water solubility. The patent also teaches that the applicable areas of use include introduction of active ingredients into toilet tanks, urinals, swimming pools, and water towers.

Isothiazolones are commonly provided in commerce in aqueous solutions, usually with inorganic, alkaline earth metal salts as a stablizer to prevent reactions which render them inactive against microorganisms. Although solid alkaline earth metal salt complexes are known (U.S. Pat. Nos. 4,150,026 and 4,241,214 mentioned above), these salt complexes suffer the disadvantage that they badly corrode processing equipment used to remove water in the course of producing the solid dry salt complex product, and the final solid salt complex product tends to be extremely dusty and thereby toxic to one during handling the product.

A typical, useful commercially available 3-isothiazolone product is Kathon ®886 (Rohm and Haas Company), a metal salt-stabilized aqueous solution of 5-chloro-2-methyl-3-isothiazolone and 2-methyl-3-isothiazolone (3:1) containing 14% active ingredient and $Mg(NO_3)_2$ plus $MgCl_2$ as stabilizers. Such commercial products suffer the disadvantages of being irritating to the skin when spilled during handling and evolving nontoxic gases which build up pressure in a sealed container provided for shipping and transportation.

Copending U.S. Ser. No. 422,495, filed Sept. 23, 1982, 1982 in the hands of the assignee common to this application, discloses that these disadvantages can be overcome by providing water-soluble microbiocidal compounds, especially 3-isothiazolones, in the form of dry solid compositions. Copending U.S. Ser. No. 422,056, filed Sept. 23, 1982, 1982 in the hands of the assignee common to this application, discloses the improvement to overcome these disadvantages by use of an article which is a flexible, water-permeable membrane containing sealed therein a composition of a water-soluble microbiocidal compound absorbed on a particulate, water-insoluble solid carrier. The present invention is a further improvement to overcome these disadvantages.

This invention is an article useful for storing, handling, transporting, and providing a microbiocidal compound at a controlled rate in a method for controlling living microorganisms in an aqueous system comprising:

(a) a flexible, water-permeable membrane having a film thickness sufficient to maintain the integrity thereof when sealed and sufficient water vapor permeability to permit diffusion of water therethrough and containing sealed therein (b) a particulate solid microbiocidal composition useful in aqueous systems comprising:

(i) about 0.1–70 weight %, based on total weight of said composition, of at least one microbiocidal compound having relatively low water solubility of less than about 1000 ppm or a combination thereof with one or more other microbiocidal compounds to give a combination characterized by a relatively low water solubility of less than about 1000 ppm; and (ii) about 99.9–30 weight %, based on total weight of said composition, of an inert, finely-divided water-insoluble solid carrier material.

It is to be understood that the total amount of microbiocidal compound in the composition can exceed the amount of compound which is soluble in the aqueous system. As the compound becomes inactive in solution, the residual undissolved compound then dissolves to maintain the concentration of microbiocidal compound up to the saturation point in the aqueous system until all of the compound is depleted.

Preferably, the flexible, water-permeable membrane used in this invention should have a film thickness of from about 0.5 mil to about 10 mils and should have a water vapor permeability of about 0.2–40 g. per ml. in 24 hrs. for a 100 in.$^2$ film. Examples of suitable film-forming materials useful in producing the flexible, water-permeable membrane include polyvinyl acetate, cellulose, cellulose acetate, polysulfone, polyester, polyamide, polyvinyl chloride, spunbonded polyethylene or low density polyethylene, polyurethane, or hot water soluble polyvinyl alcohol (PVA).

Preferably, in the particulate, solid microbiocidal composition used in the article of the invention, microbiocidal compound (i) comprises at least one water-soluble microbiocidally-effective isothiazolone, having a water solubility of less than about 1000 ppm, represented by the formula

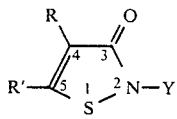

wherein

Y is an unsubstituted or substituted $C_1$–$C_{18}$ alkyl group, an unsubstituted or substituted $C_2$–$C_{18}$ alkenyl or alkynyl group, an unsubstituted or substituted $C_3$–$C_{12}$ cycloalkyl group, an unsubstituted or substituted aralkyl group of 6–10 carbon atoms, or an unsubstituted or substituted aryl group of 6–10 carbon atoms;

R is hydrogen, halogen or a $C_1$–$C_4$ alklyl group;

R' is hydrogen, halogen or a $C_1$–$C_4$ alkyl group; or

R and R' can be taken together with the C=C bond of the isothiazolone ring to form an unsubstituted or substituted benzene ring;

or at least one of said isothiazolones stabilized with at least one metal salt used in an amount of about 1–60 weight %, based on weight of isothiazolone and metal salt, said metal salt being represented by the formula:

$$(MX_n)$$

wherein

M is a cation of a metal selected from sodium, potassium, calcium, magnesium, copper, iron, zinc, barium, manganese, silver, cobalt and nickel;

X is an anion selected from chloride, bromide, iodide, sulfate, nitrate, nitrite, acetate, chlorate, perchlorate, bisulfate, bicarbonate, oxalate, maleate, p-toluene-sulfonate, carbonate, and phosphate; and n is an integer for which the anion X satisfies the valence of the cation M; and, said solid carrier material (ii) comprises an inert, finely-divided water-insoluble solid material selected from siliceous diatomaceous earth, high water absorption capacity calcium silicate granular material, charcoal, clays, vermiculite, corn cobs, wood and the like.

It is to be understood that, as the number of carbon atoms in the substituent group "Y" increases, and as halogens are substituted on the isothiazolone ring, water solubility decreases.

By a "substituted alkyl group" is meant an alkyl group having one or more of its hydrogens replaced by another substituent group. Examples of the substituted alkyl groups which characterize the isothiazolones used in this invention include hydroxyalkyl, haloalkyl, cyanoalkyl, alkylamino, dialkylamino, arylaminoalkyl, carboxyalkyl, carbalkoxyalkyl, alkoxyalkyl, aryloxyalkyl, alkylthioalkyl, arylthioalkyl, haloalkoxyalkyl, cycloaminoalkyl such as morpholinylalkyl and piperidinylalkyl and pyrrolodinylalkyl and the like, carbamoxyalkyl, alkenyl, haloalkenyl, alkynyl, haloalkynyl, isothiazolonylalkyl, and the like.

By a "substituted aralkyl group" is meant an aralkyl group having one or more of the hydrogens on either the aryl ring or the alkyl chain replaced by another substituent group. Examples of the substituted aralkyl group which characterize the isothiazolones used in this invention include halo, lower alkyl, lower alkoxy, and the like.

By a "substituted aryl group" and "substituted benzene ring" is meant an aryl group and benzene ring, respectively, such as phenyl, naphthyl, or pyridyl groups, having one or more of the hydrogens on the aryl ring replaced by another substituent group. Examples of such substituent groups include halo, nitro, lower alkyl, lower alkoxy, lower alkyland acylamino, lower carbalkoxy, sulfonyl, and the like.

By the expression "relatively low water solubility" as applied to the isothiazolones used in this invention is meant an isothiazolone or combination of isothiazolones characterized by having a water solubility of less than about 1000 ppm (0.1%). More preferably, the isothiazolone or combination thereof with other microbiocidal compounds used in this invention has a water solubility of about 500 ppm or less, most preferably about 100 ppm or less.

By the expression "microbiocidal compound" is meant those compounds effective to control those microorganisms especially of the group of bacteria, fungi (including molds and yeasts), and algae. In the method of the invention for controlling living microorganisms, by the expression "microorganisms" is meant bacteria, fungi (including molds and yeasts), and algae.

When used alone, the expression "isothiazolone(s)" is meant to include the "free" isothiazolone(s) and the metal salt complexes of the free isothiazolone(s).

More preferably, the composition used in the article of this invention comprises (i) about 1–35 weight %, based on total weight of said composition, of at least one of said isothiazolones having a water solubility of about 500 ppm or less wherein Y is an unsubstituted or substituted $C_1$–$C_{18}$ alkyl group or $C_3$–$C_{12}$ cycloalkyl group;

R is hydrogen or halogen;

R' is hydrogen or halogen; or

R and R' are taken together with the C=C bond of the isothiazolone ring to form an unsubstituted or substituted benzene ring;

or said isothiazolone stabilized with said metal salt; and (ii) about 99–65 weight%, based on total weight of said composition, of a solid carrier material selected from silicaceous diatomaceous earth, high water absorption capacity calcium silicate granular material, and clays.

Most preferably, the composition used in the article of this invention comprises (i) about 2–25 weight %, based on total weight of said composition, of at least one of said isothiazolones wherein Y is n-octyl or t-octyl, R is hydrogen and R' is hydrogen; or Y is cyclohexyl, R is chlorine and R' is chlorine; or Y is n-octyl or t-octyl, R is chlorine and R' is chlorine, or of a mixture of said isothiazolones; or said isothiazolone(s) stabilized with said metal salt wherein said metal salt is $Mg(NO_3)_2$ or a mixture of $Mg(NO_3)_2$ and $MgCl_2$; and (ii) about 98–75 weight %, based on total weight of said composition, of silicaceous diatomaceous earth.

By way of example, there may be used in combination with the above-defined most preferred, or more preferred, isothiazolones one or both of the isothiazolones having a water solubility of greater than 1000 ppm wherein Y is methyl, R is hydrogen and R' is hydrogen or chlorine, providing, of course, that the water solubility of the combination is less than about 1000 ppm.

In another aspect, the invention is a method for controlling living microorganisms in an aqueous system which comprises incorporating into the aqueous system the article of this invention containing an amount of the microbiocidal composition used in this invention sufficient to provide in the aqueous system a microbiocidally effective amount of microbiocidal compound.

In yet another aspect, the invention is a method for safening microbiocidal izothiazolone compounds which comprises preparing a sealed, flexible, water-permeable membrane having a film thickness of from about 0.5 mil to about 10 mils and having a water vapor permeability of about 0.2–40 g. per mil in 24 hr. for a 100 in.$^2$ film containing sealed therein a particulate solid microbiocidal composition comprising at least one microbiocidally effective isothiazolone (free isothiazolone or metal salt complex thereof) having a relatively low water solubility of less than about 1000 ppm or a combination thereof with one or more other microbiocidal compounds to give a combination characterized by a relatively low water solubility of less than about 1000 ppm, and an inert, finely-divided water-insoluble solid carrier material.

In still another aspect, the invention is a method for the controlled, protracted release of microbiocidal compounds, for example, microbiocidal isothiazolones, into an aqueous system by the steps of (1) preparing the article of this invention defined above; (2) introducing the article into the aqueous system; (3) permitting the aqueous system to diffuse into the article; and (4) permitting the microbiocidal compound to dissolve and to diffuse through the aqueous system; the rate of release and the concentration of microbiocidal compound in the aqueous system being controlled by the selection of the microbiocidal compound, especially the isothiazolone, used in the article of this invention having a lower or higher water solubility up to about 1000 ppm. Of course, the rate of release can also vary with the use of a flexible, water-permeable membrane having a higher or lower water vapor permeability. The concentration of the microbiocidal compound remains at the saturation level until all of the compound present in the composition is depleted.

The preparation and properties of representative isothiazolones are described in U.S. Pat. Nos. 3,517,022; 3,761,488; and 3,065,123. U.S. Pat. No. 3,849,430 further discloses a process for the preparation of representative isothiazolones. U.S. Pat. Nos. 3,870,795 and 4,067,878 describe metal salt stabilized solutions of 3-isothiazolones which are useful according to this invention. Additional isothiazolones which are useful according to the invention are those disclosed in U.S. Pat. No. 4,310,490.

The finely-divided, water-insoluble solid material can be selected from silicaceous diatomaceous earth, high water absorption capacity calcium silicate material, and clays. Suitable silicaceous diatomaceous earth material is described in the Johns-Manville Corporation Technical Bulletin FF-160A, 10-80 concerning Celite ® Diatomite Filter Aids and Natural, Calcined, and Flux-Calcined Grades thereof. Suitable high water absorption capacity calcium silicate material is commercially available under the trademark "Micro-Cel" from the Johns-Manville Corporation.

Especially preferred is a diatomaceous earth material commercially available as Celite ®545 (Johns-Manville Corporation).

Of course, conventional adjuvants and additives used in microbiocidal compositions and formulations may be incorporated into the solid microbiocidal composition by first dissolving them in the aqueous or inert organic solvent solution of the isothiazolone(s) and then blending the solution with the solid carrier material. One useful additive for use in the solid microbiocidal composition of the invention is a dye which would impart a readily visible color to the solid composition. Thus, whenever any solid microbiocidal composition would accidently be spilled onto the skin during handling, the spilled composition could readily be observed and removed before the toxicant could leach out of the solid and cause skin burns. This is in contrast to the case involving accidental spillage of the aqueous microbiocidal solution of the isothiazolone when handling in association with an aqueous system, in which case it would be difficult to distinguish between harmless aqueous system and toxic isothiazolone concentrate. Other useful adjuvants and additives include chelating agents, surfactants, dispersants, buffers, and the like.

Alternatively, other conventional adjuvants and additives used with microbiocidal compounds, such as the isothiazolones used in this invention, may be combined with the microbiocidal composition in the sealed water-permeable membrane independent of incorporation into the microbiocidal composition.

The article of the invention may be used advantageously in metal-working fluids, swimming pools, water towers such as water cooling towers, toilet bowls, washing machines, and the like. It is to be understood that, when used in washing machines, the level of isothiazolone in the article is kept at a safe, non-irritating, but microbiocidal, level.

The article according to the invention affords many advantages. One particular advantage is that the article is a solid form of the microbiocidal composition, especially isothiazolone compositions of isothiazolones known to be skin irritants, which is more convenient for handling, transporting, and shipping. The article is, therefore, also a safer form of the microbiocidal composition, especially the isothiazolone composition, in that it obviates contact of the isothiazolone composition with the skin and the leaching-out from the composition of the isothiazolone.

Another particular advantage is that the article permits the use of the solid microbiocidal composition, especially the solid isothiazolone composition, in applications in which freely-dispersed, finely-divided solid matter could not be tolerated, for example, in water cooling towers and swimming pools and the like.

For use in metal-working fluids, swimming pools, water towers, such as water cooling towers, toilet bowls, washing machines, and the like, the article of the invention can conveniently be removed from its shipping container, placed into the aqueous system to be treated, and, when the microbiocidal compound has completely leached-out of the article, the sealed membrane containing the solid carrier material can be removed by conventional techniques, for example, by hand, using tongs to dip the sealed membrane from the aqeuous system.

The following examples are illustrative of the invention and are not intended to limit it in any way. All parts and percentages are by weight unless otherwise indicated and all temperatures are in degrees Centigrade unless otherwise indicated. Percentages of the metal salts (magnesium nitrate and magnesium chloride) are based on the molecular weight of the common commercial form.

EXAMPLE 1

To 13.28 g. of Celite ®545 in each of three glass bottles was added 1 g. of the following isothiazolones in 20 ml. of methanol:

(a) 2-octyl-3-isothiazolone;
(b) 4,5-dichloro-2-cyclohexyl-3-isothiazolone; and
(c) 4,5-dichloro-2-octyl-3-isothiazolone.

Each mixture was then stirred by hand with a spatula until it appeared to be uniformly mixed and free-flowing. Air drying, to remove methanol, affords solid product, 14.28 g., containing 7 weight % of active ingredient.

1.28 g. of each of the resulting solid microbiocidal compositions was stirred in 800 ml. of deionized water. The release of active ingredient was followed by analysis of the supernatant water by ultraviolet spectroscopy. Total release of active ingredient would give 112 ppm. The results are set forth in the following table.

| Compound | Water Solubility | Concentration in Solution at Elasped Time | | | |
|---|---|---|---|---|---|
| | | 0.75 hr. | 3.0 hr. | 23.0 hr. | 66.0 hr. |
| A | 500 ppm | 106 ppm | 112 ppm | — | — |
| B | 40 ppm | 27 ppm | 39 ppm | — | 39 ppm |
| C | 14 ppm | 7 ppm | 10 ppm | 14 ppm | 14 ppm |

The data above show that the time required to reach a saturated solution of compound A is less than 1 hour, of compound B is between 1-3 hours, and of compound C is between 6 and 24 hours.

EXAMPLE 2

A solid microbiocidal composition containing 20 weight % of active ingredient was prepared by dissolving 2.66 g. of crystalline 2-octyl-3-isothiazolone in 15 ml. of methanol. To this solution there was added 0.6 g. of Mg(NO$_3$)$_2$.6 H$_2$O. The resulting solution was added to 10 g. of Celite 545 in a 4 fl. oz. bottle and the mixture was stirred by hand using a spatula until it appeared to be uniformly mixed and free-flowing. Methanol was removed by air-drying (or by heating the mixture under reduced pressure), and a uniform, free-flowing particulate solid was obtained.

Compositions containing 20 weight % of 4,5-dichloro-2-cyclohexyl-3-isothiazolone and 4,5-dichloro-2-octyl-3-isothiazolone were prepared as described above.

EXAMPLE 3

There was sealed in bags of 3-mil cellulose film (3.5 in.$^2$ surface area) 1.28 g. of each of the three compositions prepared in Example 1 containing compounds A, B, and C, respectively. For comparison, 1.28 g. of a 7% active ingredient solid composition of Kathon ®886 (a 3:1 weight ratio blend of 5-chloro-2-methyl-3-isothiazolone and 2-methyl-3-isothiazolone with 15 weight % of Mg(NO$_3$)$_2$ and 9 weight % of MgCl$_2$ in aqueous solution containing 14% active ingredient available from the Rohm and Haas Company) absorbed on Celite ®545 was sealed in a bag of 3-mil cellulose film (3.5 in.$^2$ surface area). The rate of release and concentration of active ingredient from the sealed bags into 800 ml. of deionized water was followed by ultraviolet spectroscopy. The results are set forth in the following table. Complete release of active ingredient from each sample would give 112 ppm.

| | Concentration/Rate of Release (Water Solubility, ppm) | | | |
|---|---|---|---|---|
| Time Interval | Kathon ® 886 (140,000 ppm) | Compound A (500 ppm) | Compound B (42 ppm) | Compound C (14 ppm) |
| 1 day | 90 ppm | 27 ppm | 5 ppm | 0.4 ppm |
| 2 days | 112 ppm | — | — | — |
| 5 days | — | 82 ppm | 11 ppm | 1.7 ppm |

These data illustrate that the article according to this invention provides a protracted release of a microbiocidally-effective amount of isothiazolone over a period of 1-5 days and longer.

What is claimed is:

1. An article useful for storing, handling, transporting, and providing a microbiocidal compound at a controlled rate in a method for controlling living microorganisms in an aqueous system comprising (a) a flexible, water-permeable membrane having a film thickness sufficient to maintain the integrity thereof when sealed and sufficient water vapor permeability to permit diffusion of water therethrough and containing sealed therein (b) a particulate solid microbiocidal composition useful in aqueous systems comprising:

(i) about 0.1-70 weight %, based on total weight of said composition, of at least one water-soluble microbiocidal compound having a relatively low water solubility of less than about 1000 ppm or a combination thereof with one or more other microbiocidal compounds to give a combination characterized by a relatively low water solubility of less than about 1000 ppm; and (ii) about 99.9–30 weight %, based on total weight of said composition, of an inert, finely-divided water-insoluble solid carrier material.

2. An article according to claim 1 wherein the flexible, water-permeable membrane has a film thickness of about 0.5 mil to about 10 mils and has a water vapor permeability of about 0.2–40 g. per ml. in 24 hrs. for a 100 in.$^2$ film.

3. An article according to claim 2 wherein said flexible, water-permeable membrane is produced from a film-forming material selected from hot water soluble polyvinyl alcohol (PVA), polyvinyl acetate, cellulose, cellulose acetate, polysulfone, polyester, polyamide, polyvinyl chloride, spunbonded polyethylene, low-density polyethylene or polyurethane.

4. An article according to claim 2 wherein said composition (b) comprises, as said microbiocidal compound (i), at least one microbiocidally-effective isothiazolone, having a relatively low water solubility of less than about 1000 ppm, represented by the formula:

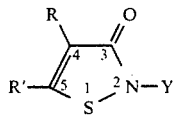

wherein

Y is an unsubstituted or substituted $C_1$–$C_{18}$ alkyl group, an unsubstituted or substituted $C_2$–$C_{18}$ alkenyl or alkynyl group, an unsubstituted or substituted $C_3$–$C_{12}$ cycloalkyl group, an unsubstituted or substituted aralkyl group of 6–10 carbon atoms, or an unsubstituted or substituted aryl group of 6–10 carbon atoms;

R is hydrogen, halogen or a $C_1$–$C_4$ alkyl group;

R' is hydrogen, halogen or a $C_1$–$C_4$ alkyl group; or

R and R' can be taken together with the C=C bond of the isothiazolone ring to form an unsubstituted or substituted benzene ring;

or at least one of said isothiazolones stabilized with at least one metal salt used in an amount of about 1–60 weight %, based on weight of 3-isothiazolone and metal salt, said metal salt being represented by the formula:

$$(MX_n)$$

wherein

M is a cation of a metal selected from sodium, potassium, calcium, magnesium, copper, iron, zinc, barium, manganese, silver, cobalt and nickel;

X is an anion selected from chloride, bromide, iodide, sulfate, nitrate, nitrite, acetate, chlorate, perchlorate, bisulfate, bicarbonate, oxalate, maleate, p-toluene-sulfonate, carbonate, and phosphate; and n is an integer for which the anion X satisfies the valence of the cation M; and, as said solid carrier material (ii), an inert, finely-divided water-insoluble solid material selected from siliceous diatomaceous earth, high water absorption capacity calcium silicate granular material, clays, charcoal, vermiculite, corn cobs, and wood.

5. An article according to claim 4 wherein said composition (b) comprises (i) about 1–35 weight %, based on total weight of said composition, of said isothiazolone having a water solubility of about 500 ppm or less wherein Y is an unsubstituted or substituted $C_1$–$C_{18}$ alkyl group or $C_3$–$C_{12}$ cycloalkyl group;

R is hydrogen or halogen;

R' is hydrogen or halogen; or

R and R' are taken together with the C=C bond of the 3-isothiazolone ring to form an unsubstituted or substituted benzene ring;

or said isothiazolone stabilized with said metal salt; and (ii) about 99–65 weight %, based on total weight of said composition, of said solid carrier material selected from siliceous diatomaceous earth, high water absorption capacity calcium silicate granular material, and clays.

6. An article according to claim 5 wherein said composition (b) comprises (i) about 2–25 weight %, based on total weight of said composition, of said isothiazolone wherein Y is n-octyl or t-octyl, R is hydrogen and R' is hydrogen, or said isothiazolone stabilized with said metal salt wherein said metal salt is $Mg(NO_3)_2$ or a mixture of $Mg(NO_3)_2$ and $MgCl_2$; and (ii) about 98–75 weight %, based on total weight of said composition, of siliceous diatomaceous earth.

7. An article according to claim 5 wherein said composition (b) comprises (i) about 2–25 weight %, based on total weight of said composition, of said isothiazolone wherein Y is cyclohexyl, R is chlorine and R' is chlorine, or said isothiazolone stabilized with said metal salt wherein said metal salt is $Mg(NO_3)_2$ or a mixture of $Mg(NO)_2$ and $MgCl_2$; and (ii) about 98–75 weight %, based on total weight of said composition, of siliceous diatomaceous earth.

8. An article according to claim 5 wherein said composition (b) comprises (i) about 2–25 weight %, based on total weight of said composition, of said isothiazolone wherein Y is n-octyl or t-octyl, R is chlorine and R' is chlorine, or said isothiazolone stabilized with said metal salt wherein said metal salt is $Mg(NO_3)_2$ or a mixture of $Mg(NO_3)_2$ and $MgCl_2$; and (ii) about 98–75 weight %, based on total weight of said composition, of siliceous diatomaceous earth.

9. An article according to claim 5 wherein said isothiazolone is provided in an aqueous solution.

10. An article according to claim 5 wherein said composition (b) comprises (i), in combination with said isothiazolone having low water solubility, one or both of the isothiazolones having a water solubility of greater than about 1000 ppm wherein Y is methyl, and R is hydrogen and R' is hydrogen or chlorine, or an aqueous solution of said combination of isothiazolones stabilized with said metal salt wherein said metal salt is $Mg(NO_3)_2$ or a mixture of $Mg(NO_3)_2$ and $MgCl_2$, the combination comprising about 2–25 weight %, based on total weight of said composition; and (ii) about 98–75 weight %, based on total weight of said composition, of siliceous diatomaceous earth.

* * * * *